(12) United States Patent
Zhao et al.

(10) Patent No.: US 11,149,293 B2
(45) Date of Patent: Oct. 19, 2021

(54) FERMENTATION METHOD FOR PRODUCING GELLAN GUM

(71) Applicants: Zhejiang DSM Zhongken Biotechnology Co. Ltd, Zhejiang (CN); DSM IP Assets B.V., Te Heerlen (NL)

(72) Inventors: Jie Zhao, Shanghai (CN); Wouter Adrianus Van Winden, Ac Echt (NL); Rogier Meulenberg, Aa Echt (NL); Zhihui Gao, Shanghai (CN)

(73) Assignees: Zhejiang DSM Zhongken Biotechnology Co. Ltd, Zhejiang (CN); DSM IP Assets B.V., Te Heerlen (NL)

(*) Notice: Subject to any disclaimer, the term of this patent is extended or adjusted under 35 U.S.C. 154(b) by 0 days.

(21) Appl. No.: 16/178,438

(22) Filed: Nov. 1, 2018

(65) Prior Publication Data

US 2019/0144903 A1    May 16, 2019

(30) Foreign Application Priority Data

Nov. 10, 2017 (CN) .......................... 201711111402.9

(51) Int. Cl.
*C12P 19/04* (2006.01)
*C12N 1/20* (2006.01)

(52) U.S. Cl.
CPC ............... *C12P 19/04* (2013.01); *C12N 1/20* (2013.01)

(58) Field of Classification Search
CPC .................................. C12P 19/04; C12N 1/20
See application file for complete search history.

(56) References Cited

U.S. PATENT DOCUMENTS

| 7,645,600 | B2 * | 1/2010 | Yamazaki | C12P 19/04 435/183 |
| 8,685,698 | B2 * | 4/2014 | Wu | C12R 1/01 435/101 |
| 2006/0019354 | A1 | 1/2006 | Yamazaki | |
| 2016/0108452 | A1 * | 4/2016 | Sun | C12P 7/6463 435/39 |
| 2016/0122787 | A1 * | 5/2016 | Simpson | C12P 7/6427 435/134 |

FOREIGN PATENT DOCUMENTS

| CN | 1635132 | A | | 7/2005 |
| CN | 101072873 | A | | 11/2007 |
| CN | 101544993 | A | | 9/2009 |
| CN | 101586135 | | * | 11/2009 |
| CN | 101586135 | A | | 11/2009 |
| CN | 191586135 | A | | 11/2009 |
| CN | 102747016 | A | | 10/2012 |
| CN | 105820950 | A | | 8/2016 |
| CN | 106687605 | A | | 5/2017 |
| EP | 2360238 | A1 | | 8/2011 |

OTHER PUBLICATIONS

Li et al. "Optimization of Bioethanol Production in Fed-Batch Fermentation" 8th IFAC Symposium on Advanced Control of Chemical Processes, Jul. 10-13, 2012 (Year: 2012).*
Chang et al. "Multistage high cell continuous fermentation for high productivity and titer" Bioprocesses Biosyst Eng 34: 419-431 (Year: 2011).*
Database WPI, Week 201001, Thomson Scientific, London, GB; AN 2009-S02872, XP002799600.
Extended European Search Report, EP 18205490.8, dated Mar. 22, 2019.
Giavasis, Ioannis, et al., "Gellam Gum", CRC Critical Reviews in Biotechnlogy, vol. 20, No. 3, 2000, pp. 177-211, XP055567240.
The Office Action issued by the China National Intellectual Property Administration (CNIPA) dated Jul. 31, 2020 for the Chinese Patent Application No. 201711111402.9.
The Second Office Action issued by the China National Intellectual Property Administration (CNIPA) dated Apr. 2, 2021 for the corresponding Chinese Patent Application No. 201711111402.9.
Cai, "Shortening fermentation cycle and increasing loading rate—Experiment of replacing seed culture with fermentation broth", Fermentation Technology Communication, vol. 17, Issue No. 2, published on Jun. 30, 1988 (the cited reference (Nonpatent 1) in the Office Action issued by the CNIPA dated Apr. 2, 2021 for the corresponding Chinese Patent Application No. 201711111402.9.

* cited by examiner

*Primary Examiner* — Blaine Lankford
*Assistant Examiner* — Lauren K Van Buren
(74) *Attorney, Agent, or Firm* — Maschoff Brennan; Brent A. Johnson; Yuefen Zhou

(57) ABSTRACT

This invention provides a fermentation method of producing gellan gum, wherein a certain amount of fermentation broth is retained in the fermentor as a seed for next batch fermentation or transferred to another fermentor as a seed for next batch fermentation in that fermentor. The fermentation method of this invention reduces fermentation cost of gellan gum and lowers contamination risk during seed cultivation.

12 Claims, No Drawings

FERMENTATION METHOD FOR PRODUCING GELLAN GUM

CROSS-REFERENCE TO RELATED APPLICATION

This application claims priority to the Chinese Patent Application No. 201711111402.9, filed Nov. 10, 2017, which is incorporated by reference by its entirety.

TECHNICAL FIELD

This invention is related to the field of biological fermentation. Specifically, this invention is related to a fermentation method of producing gellan gum.

BACKGROUND

Gellan gum is a microbial polysaccharide generated by for example *Sphingomonas* sp. Gellan gum is widely used in food, pharmaceutical, chemical engineering and other industries due to its low dosage, good compatibility, and resistance to acid, high temperature and enzyme, etc.

Gellan gum is mainly produced through batch fermentation of microorganisms, which includes preparing a medium containing carbon sources, nitrogen sources, inorganic salts and other required nutrient substances before inoculation, and after high temperature sterilization, inoculating with a new seed to start fermentation. In such a traditional batch fermentation method, a separate seed fermentor is required for seeds cultivation and preparation. The cultivated seeds are then transferred into production fermentors under strict aseptic conditions, which involves complicated processing steps, and results in higher costs and contamination risk.

During gellan gum fermentation, a part of the nutrients that are dosed is used by microorganisms to reproduce and form more biomass. This consumption of nutrients forms a cost of the fermentation but does not give revenues. On the contrary, costs are also made to discard produced biomass.

Therefore, removal or simplification of the seed culturing steps in high-viscosity fermentation of gellan gum, and reuse of the biomass can significantly enhance productivity, while decrease fermentation and waste disposal costs, and lower the contamination risk.

DETAILED DESCRIPTION

This invention provides a fermentation method of producing gellan gum. Specifically, the said fermentation method of producing gellan gum includes using a certain amount of fermentation broth as a seed for next batch fermentation.

In this invention, the "fermentation broth" means the medium inoculated with strains that are able to produce gellan gum products and cultivated for a period of time and then containing gellan gum and strains. The said strains include but are not limited to *Sphingomonas paucimobilis*, *Sphingomonas azotofigens* and *Sphingomonas elodea*. In this invention, the said medium means any mediums containing carbon sources, nitrogen sources, phosphates and inorganic salts applicable for cultivating the microorganisms to ferment and produce gellan gum.

In this invention, the fermentation broth can be used as a seed for next batch fermentation as follows: after the fermentation ends, retaining a certain amount of the fermentation broth in a fermentor as the seed for the next batch fermentation, harvesting the remaining fermentation broth for separation and purification steps of gellan gum, and then feeding sterilized medium directly into the same fermentor to start the next batch fermentation. Therefore, the said fermentation method of producing gellan gum can include the following steps:
1) Strain activation;
2) Inoculating the activated strain into the medium in a fermentor, starting fermentation;
3) After the fermentation ends, retaining a certain amount of fermentation broth in the fermentor as a seed for next batch fermentation, and the remaining fermentation broth is harvested for separation and purification steps of gellan gum;
4) Adding medium to the seed retained in Step 3) to start the next batch fermentation; and
5) Optionally, repeating step 3) and step 4).

In this invention, optionally, the fermentation broth can also be used as a seed for next batch fermentation as follows: during the fermentation, taking a certain amount of fermentation broth from a fermentor as the seed, which is then transferred into another fermentor containing sterilized medium to start the next batch fermentation, and the remaining fermentation broth continues fermenting. During the fermentation, preferably, the certain amount of fermentation broth can be taken from the fermentor as the seed from 5 hours to the end of the fermentation, more preferably, from 20 hours to 48 hours, most preferably, from 36 hours to 48 hours.

Therefore, the said fermentation method of producing gellan gum can also include the following steps:
1) Strain activation;
2) Inoculating the activated strain into the medium in a fermentor, starting fermentation;
3) During the fermentation, preferably from 5 hours to the end of fermentation, more preferably from 20 hours to 48 hours, most preferably from 36 hours to 48 hours, taking a certain amount of fermentation broth as a seed, while the remaining broth continues fermenting;
4) Inoculating the seed obtained from Step 3) into next batch of medium to start the fermentation; and
5) Optionally, repeating step 3) and step 4).

It is well-known in the art that the strain activation generally refers to the process of inoculating the strains preserved in glycerin tubes or on culture-medium slants into a seed medium to cultivate under certain conditions to enhance the biomass growth of the strains. The activated strains can be transferred into production fermentors for fermentation and producing gellan gum.

In this invention, the step 3) and step 4) can be repeated any number of times. The strain activation can be started according to the actual situation of the fermentation. Preferably, the step 3) and step 4) are repeated 1-25 times, more preferably, are repeated 2-10 times. In this invention, "a certain amount" can be any proportion based on the total volume of the fermentation broth. The said certain amount only affects the fermentation cycles of the following batches, but does not affect the consumption of nutrients, the final content of gellan gum, or the conversion rate of sugar to gum after the fermentation. The optimal amount can be selected based on the productivity and the batch yield. Preferably, the certain amount is 3-50% of the total volume of the fermentation broth, more preferably 4-25%, most preferably 5-10%.

In this invention, the certain amount of fermentation broth can be used as the seed for the next batch fermentation as such, i.e. without any further processing of the broth such as separation of the cells from the fermentation broth.

It can be understood by person skilled in the art that the certain amount of fermentation broth can be taken and simply treated before being used as the seed for the next batch fermentation, i.e. by adjusting pH, adding nutrients such as carbon source, and/or diluting with water, etc.

In this invention, the fermentation can be a batch fermentation with one-time feeding in of all the medium, or can be a fed batch fermentation with restricted controlling of key nutrient sources, such as nitrogen-feed fermentation (see patent application with the number of CN201710518726.8).

In this invention, the fermentation method of producing gellan gum can also include separation and purification steps of gellan gum. The separation and purification method of gellan gum is well-known in the art, thus no further detailed description is made in this application. For more details, see Ioannis Giavasis etc., Critical Reviews in Biotechnology, 20 (3): 177-211 (2000).

In this invention, a certain amount of fermentation broth is used as a seed for next batch fermentation in high-viscosity fermentation of gellan gum. This fermentation method simplifies seed cultivation process, saves seed cultivation equipment and raw materials, decreases contamination risk during seed cultivation, shortens production cycles, lowers fermentation cost (i.e. seed cultivation, sterilization, waste disposal), enhances productivity, and achieves unexpected effects.

Further descriptions are given in this invention by the following examples. These examples are just for illustration instead of restricting the scope of this invention.

EXAMPLES

In gellan gum production, two indicators are commonly used to evaluate the fermentation levels: the content of gellan gum in the fermentation broth (g/kg fermentation broth); the viscosity of the fermentation broth (cP) at a given shear rate. Generally, a higher fermentation level is indicated by a higher content of gellan gum in the fermentation broth and a higher viscosity of the fermentation broth. In this invention, the above-mentioned indicators were determined to evaluate the fermentation levels of the fermentation method.

Example 1

1) Medium Preparation

Seed medium: seed medium was prepared as per the following composition: 7 g/Kg yeast extract, 25 g/Kg sucrose, 0.5 g/Kg KH$_2$PO$_4$, 0.75 g/Kg K$_2$HPO$_4$ and 0.6 g/Kg MgSO$_4$.7H$_2$O. The medium was adjusted to pH 7.0±0.1 and sterilized.

Fermentation medium: 7.5 fermentation medium in 12 fermentor was prepared as per the following composition: 15 g/kg glucose, 2.5 g/kg soy protein isolate, 0.5 g/kg KH$_2$PO$_4$, 0.5 g/kg K$_2$HPO$_4$, 0.375 g/kg MgSO$_4$.7H$_2$O and 0.15 g/kg antifoaming agent. The medium was adjusted to pH 7.0±0.1 and sterilized.

2) Strain Activation

*Sphingomonas azotofigens* (Zhejiang DSM Zhongken Biotechnology Co., Ltd.) was inoculated into a 500 mL shaking flask filled with 50 ml sterilized seed medium and cultivated on cultivation shaker under 30° C., 200 RPM for 16 hours; then 10 ml culture was taken and inoculated into a 2 L shaking flask filled with 450 mL sterilized seed medium, and cultivated for 16 hours as activated seed for Round 1 fermentation.

3) Fermentation Process Control

In Round 1 fermentation, 375 g activated seed obtained from Step 2) was inoculated into a 12 L fermentor filled with 7.5 L sterilized fermentation medium to implement fermentation as per the following process conditions listed in Table 1:

TABLE 1

| Process parameters | Fermentation time (h) | Parameter control |
|---|---|---|
| Temperature [° C.] | 0 - End of fermentation | 30.0 ± 0.1 |
| Ventilation (L/min) | 0-12 | 4 |
|  | 12 - End of fermentation | 8 |
| pH | 0 - End of fermentation | 7.0 ± 0.1 |
| Speed of stirring [rpm] | 0-24 | 600 → 1000 |
|  | 24 - End of fermentation | 1000 |

At 36 hours after the start of the Round 1 fermentation, 750 g fermentation broth was taken from the Round 1 fermentor and inoculated into a 12 L fermentor filled with 7.5 L sterilized fermentation medium to implement Round 2 fermentation, under the same process conditions as above;

At 36 hours after the start of the Round 2 fermentation, 750 g fermentation broth was taken from the Round 2 fermentor and inoculated into a 12 L fermentor filled with 7.5 L sterilized fermentation medium to implement Round 3 fermentation, under the same process conditions as above;

At 36 hours after the start of the Round 3 fermentation, 750 g fermentation broth was taken from the Round 3 fermentor and inoculated into a 12 L fermentor filled with 7.5 L sterilized fermentation medium to implement Round 4 fermentation, under the same process conditions as above;

All the four rounds of fermentation were finished 48 hours after the start of fermentation.

4) Fermentation Results

After 48 hours of fermentation, the contents of gellan gum and the viscosities were measured. The results were shown as follows in Table 2:

TABLE 2

|  | Round 1 | Round 2 | Round 3 | Round 4 |
|---|---|---|---|---|
| Content of gellan gum (g/kg) | 5.04 | 5.45 | 5.97 | 5.46 |
| Viscosity (cP) | 4720 | 5934 | 5670 | 4920 |

The content of gellan gum was measured by common ethanol precipitation method; the viscosity of fresh fermentation broth sample was directly measured with a rheometer (Anton Paar MCR 301) with the CP50-1 spindle for 5 minutes under a constant shear rate of 10 s$^{-1}$ and a constant temperature of 30° C.

Example 2

1) Medium Preparation

The preparation of seed medium was the same as Example 1.

Fermentation medium: 7.5 L fermentation medium in 12 L fermentor was prepared as per the following composition: 15 g/kg glucose, 0.4 g/kg monosodium glutamate, 0.4 g/kg yeast extract, 0.5 g/kg KH$_2$PO$_4$, 0.5 g/kg K$_2$HPO$_4$, 0.375 g/kg MgSO$_4$.7H$_2$O, 0.5 g/Kg microelement solution (5 g/kg Citric acid.1H$_2$O, 0.20 g/kg H$_3$BO$_3$, 0.20 g/kg CuCl$_2$.2H$_2$O, 0.20 g/kg NiCl$_2$.6H$_2$O, 0.60 g/kg MnSO$_4$.1H$_2$O, 0.025 g/kg Na$_2$MoO$_4$.2H$_2$O, 1.0 g/kg ZnSO$_4$.7H$_2$O, 8 g/kg FeSO$_4$.7H$_2$O) and 0.15 g/kg antifoaming agent. The medium was adjusted to pH 7.0±0.1 and sterilized.

2) Nitrogen Source 500 mL solution was prepared, which contained 1.5 g/Kg monosodium glutamate and 1.5 g/Kg liquid yeast extract, and used as supplementary nitrogen source after sterilization.

3) Strain Activation was the Same as Step 2) in Example 1

4) Fermentation Process Control

In Round 1 fermentation, 375 g activated seed obtained from Step 3) was inoculated into a 12 L fermentor filled with 7.5 L sterilized fermentation medium to implement fermentation as per the following process conditions, and the supplementary nitrogen source was fed at the constant speed shown below in Table 3:

TABLE 3

| Process parameters | Fermentation time (h) | Parameter control |
|---|---|---|
| Temperature [° C.] | 0 - End of fermentation | 30.0 ± 0.1 |
| Ventilation (L/min) | 0-12 | 4 |
|  | 12 - End of fermentation | 8 |
| pH | 0 - End of fermentation | 7.0 ± 0.1 |
| Speed of stirring [rpm] | 0-24 | 600 → 1000 |
|  | 24 - End of fermentation | 1000 |
| Feeding rate of nitrogen source (g/h) | 0 - End of fermentation | 7 |

After the Round 1 fermentation was finished, 375 g fermentation broth was taken from the Round 1 fermentor and inoculated into a 12 L fermentor filled with 7.5 L sterilized fermentation medium to implement Round 2 fermentation, under the same process conditions and nitrogen source control as the Round 1 fermentation;

Both rounds of fermentation were finished 48 hours after the start of fermentation.

5) Fermentation Results

After 48 hours of fermentation, the contents of gellan gum and viscosities were measured with the same methods as Example 1. The results were shown as follows in Table 4:

TABLE 4

|  | Round 1 | Round 2 |
|---|---|---|
| Content of gellan gum (g/kg) | 5.22 | 5.1 |
| Viscosity (cP) | 4620 | 4350 |

The invention claimed is:

1. A high-viscosity fermentation method of producing gellan gum comprising the following steps:
   1) activating a strain;
   2) Inoculating the activated strain into a medium in a fermentor, starting a first fermentation;
   3) After the first fermentation ends, retaining a certain amount of a fermentation broth from the first fermentation in the fermentor as a seed to be directly used in a next batch fermentation in the same fermentor, and the remaining fermentation broth of the first fermentation is harvested for separation and purification of gellan gum, wherein the certain amount of the fermentation broth retained from the first fermentation to be directly used as the seed in the next batch fermentation is equivalent to 3% to 50% the total volume of the fermentation broth of the first fermentation in the fermentor before the gellan gum is harvested;
   4) Adding a medium into the seed retained in Step 3 in the fermentor to start the next batch fermentation; and
   wherein the first fermentation and the next batch fermentation are high-viscosity fermentation.

2. The fermentation method according to claim 1, characterized in that, the certain amount of the fermentation broth from the first fermentation to be directly used as the seed in the next batch fermentation is corresponding to 4% to 25% the total volume of the fermentation broth.

3. The fermentation method according to claim 1, characterized in that, the certain amount of the fermentation broth from the first fermentation to be directly used as the seed in the next batch fermentation is 5% to 10% the total volume of the fermentation broth.

4. The fermentation method according to claim 1, further comprises separation and purification of the gellan gum obtained from the next batch fermentation in step 4 of claim 1.

5. The fermentation method according to claim 1, wherein the fermentation is a batch fermentation or a fed batch fermentation.

6. A high-viscosity fermentation method of producing gellan gum comprising the following steps:
   1) activating a strain;
   2) Inoculating the activated strain into a medium in a fermentor, and starting a first fermentation;
   3) During the first fermentation, from 5 hours after starting the fermentation to the end of the fermentation, taking out a certain amount of a fermentation broth from the first fermentation from the fermentor as a seed to be directly used in a next batch fermentation in another fermentor, while the remaining fermentation broth of the first fermentation continues fermenting, wherein the certain amount of the first fermentation broth taken out as the seed to be directly used in the next batch fermentation is equivalent to 3% to 50% the total volume of the fermentation broth of the first fermentation before the seed is taken out;
   4) Adding the seed obtained from Step 3 into the next batch of medium in another fermentor to start the next batch fermentation; and
   wherein the first fermentation and the next batch fermentation are high-viscosity fermentation.

7. The fermentation method according to claim 6, wherein, in step 3, during the fermentation, from 20 hours to 48 hours after starting the fermentation, taking out the certain amount of the fermentation broth from the first fermentation to be directly used as the seed in the next batch fermentation, while the remaining broth continues fermenting.

8. The fermentation method according to claim 6, wherein, in step 3, during the fermentation, from 36 hours to 48 hours after starting the fermentation, taking out the certain amount of the fermentation broth from the first fermentation to be directly used as the seed in the next batch fermentation, while the remaining broth continues fermenting.

9. The fermentation method according to claim 6, wherein the certain amount of the fermentation broth from the first fermentation to be directly used as the seed in the next batch fermentation is corresponding to 4% to 25% the total volume of the fermentation broth.

10. The fermentation method according to claim 6, wherein the certain amount of the fermentation broth from the first fermentation to be directly used as the seed in the next batch fermentation is 5% to 10% the total volume of the fermentation broth.

11. The fermentation method according to claim 6, further comprises separation and purification of the gellan gum obtained from the first fermentation.

12. The fermentation method according to claim 6, wherein the fermentation is a batch fermentation or a fed batch fermentation.

\* \* \* \* \*